(12) United States Patent
Ekhart et al.

(10) Patent No.: US 9,040,571 B2
(45) Date of Patent: May 26, 2015

(54) VETERINARY FORMULATION FOR ADMINISTRATION OF A WATER-INSOLUBLE DRUG TO A TARGET ANIMAL THROUGH A WATER DISTRIBUTION SYSTEM

(75) Inventors: Peter Frank Ekhart, Amsterdam (NL); Mario Van Wandelen, Zeist (NL); Jan Matthijs Jetten, Zeist (NL)

(73) Assignee: Elanco Animal Health Ireland Limited, Sligo (IE)

( * ) Notice: Subject to any disclaimer, the term of this patent is extended or adjusted under 35 U.S.C. 154(b) by 1442 days.

(21) Appl. No.: 12/259,844

(22) Filed: Oct. 28, 2008

(65) Prior Publication Data

US 2009/0062362 A1 Mar. 5, 2009

Related U.S. Application Data

(63) Continuation of application No. 10/069,673, filed as application No. PCT/NL00/00596 on Aug. 28, 2000, now abandoned.

(30) Foreign Application Priority Data

Sep. 3, 1999 (EP) .................................... 99202876

(51) Int. Cl.
| | |
|---|---|
| *A01N 43/52* | (2006.01) |
| *A61K 31/415* | (2006.01) |
| *A61K 9/107* | (2006.01) |
| *A61K 47/36* | (2006.01) |
| *A61K 47/44* | (2006.01) |

(52) U.S. Cl.
CPC ............ *A61K 9/1075* (2013.01); *A61K 31/415* (2013.01); *A61K 47/36* (2013.01); *A61K 47/44* (2013.01)

(58) Field of Classification Search
USPC ........................................... 514/393
See application file for complete search history.

(56) References Cited

FOREIGN PATENT DOCUMENTS

| FR | 2 336 931 A1 | 7/1977 |
| FR | 2336931 | * 7/1977 |
| WO | WO 95/13065 A1 | 5/1995 |
| WO | WO 95/23590 A1 | 9/1995 |

OTHER PUBLICATIONS

The Merck Index, 12th Edition 1996; Benzyl Alcohol-1159; Isopropyl Myristate-5234; Flubendazole-4154; Fenbendazole-4000; Oxfendazole-7069.*
Lur'e et al. Vegetable oils for enhancement of mebendazole bioavailability (on an experimental model of *Echinococcus multilocularis*) Meditsinskaya Parazitologiiya i Parazitarnye Bolezni 1987 (2).
Hill R.L., "Detergents in Agrochemical and Pesticide Applications," in Handbook of Detergents, Part E: Applications, Zoller, ed., 2009, CRC Press, Boca Raton, FL, pp. 315-316.

* cited by examiner

*Primary Examiner* — Robert A Wax
(74) *Attorney, Agent, or Firm* — James J. Sales; Elizabeth A. McGraw

(57) ABSTRACT

This invention concerns a method for the preparation of a suspoemulsion formulation, which can be easily produced on an industrial scale and which allows the reproducible and effective administration of one or more water-insoluble veterinary drugs through water distribution systems. The water-insoluble veterinary drug, in finely ground form, is dispersed in a water immiscible liquid, followed by homogenization of this system into a water phase. To facilitate the preparation of a stable formulation, one or more stabilizing agents such as emulsifiers, thickeners, anti-oxidants and anti-microbials can be used. The resulting suspoemulsion shows excellent long term storage stability and a good "in use" stability after dilution in a vessel and during all handling and transport in the water distribution system.

8 Claims, No Drawings

VETERINARY FORMULATION FOR ADMINISTRATION OF A WATER-INSOLUBLE DRUG TO A TARGET ANIMAL THROUGH A WATER DISTRIBUTION SYSTEM

CROSS REFERENCE TO RELATED APPLICATIONS

This is a continuation application of and claims priority to U.S. application Ser. No. 10/069,673 filed Oct. 15, 2002 now abandoned, which is the national stage of Application No. PCT/NL00/00596, filed Aug. 28, 2000 which application claims priority from EP 99202876.1, filed Sep. 3, 1999 the contents of which are hereby incorporated by reference.

The present invention relates to a method for preparing a veterinary composition comprising a water-insoluble veterinarily active compound, especially a benzimidazole anthelmintic, suitable for administering to a target animal through a water distribution system for the purpose of therapeutic and prophylactic medication.

BACKGROUND OF THE INVENTION

Parasitic infections continue to be an important problem in animal production. Prophylactic or therapeutic use of anthelmintic drugs is a standard practice for every farm, where pigs or all kinds of poultry species are reared. The requirements for an anthelmintic product that is suitable for use in the intensive pig and poultry industry are: a broad spectrum activity (active against all important worm species that can occur in pigs), potent activity against the adult as well as the larval stages of the worms and the products should also have a wide safety margin.

For pig production 3 main groups of products are used:
 imidathiazoles (levamisole).
 avermectins (ivermectin, doramectin,
 benzimidazoles (flubendazole, fenbendazole, mebendazole, oxfendazole, albendazole, cambendazole, parbendazole, oxibendazole and cyclobendazole), and pro-benzimidazoles (febantel, thiophanate and netobimin).

For the poultry industry the avermectins are excluded because of specific toxicity reasons and the choice is therefore largely limited to levamisole and a few benzimidazole compounds.

The administration of benzimidazole compounds to pigs and poultry has so far been limited to oral administration as a top dressing on the feed or admixed into the feed. Benzimidazoles are insoluble in water and therefore their administration via the drinking water has been virtually impossible.

Medication via drinking water is routinely used for prophylaxis and treatment of infectious diseases of intensively reared animals. The increased flexibility offered by medicating via water as compared to either parenteral or in-feed medication makes it an attractive alternative.

With drinking water treatment the major drawbacks of in-feed medication can be avoided:
 medicated feed may not be immediately available when animals are sick
 poor homogeneity of mix
 segregation from feed during transport
 variable individual intake
 requires bulk storage
 cross contamination (carry-over) of feed batches at the feed mill
 difficult to manage withdrawal times
 no flexibility in treatment and dosage schedules
 sick animals stop eating and therefore stop taking the necessary mounts of medication.

The effectiveness of medication via the drinking water largely depends on the quality of the formulation and the palatability of the medication. Such formulation should provide:
 maximum availability of the drug
 minimal segregation of the active compound in the water delivery systems, medication pumps, nipples, cups . . . etc.
 a very precise dosing and homogeneous distribution in the water
 a guaranteed stability of the active compound, irrespective of the quality of the water used.

Many pig and poultry farms are already equipped with the necessary devices to administer the medication via drinking water. Such water delivery systems on farms are complex systems of tanks, pipes, coils, pen drinkers and nipples. An average stable may contain several hundreds of meters of pipes with many coils and hundreds of individual cups and/or nipples. The water in the watering system in a pig or poultry house obeys the principles of laminar flow through the pipes and coils and is subjected to the so called "shearing" forces which will affect the rate of flow. In such complex piping system there are considerable risks for segregation or sedimentation of the medication, certainly when it concerns water insoluble compounds.

The quality of the drinking water will vary considerably from region to region, some farmers even might use their own water supplies. This can have a very significant impact on the solubility or dispersibility of the medication into the drinking water.

Some products currently used in the drinking water (e.g. oxytetracycline) are not very readily soluble and solubility enhancing agents such as citric acid are often used to increase the solubility. It is known however that the use of citrate-based compounds may dislodge sediment and result in blocked nipples or drinkers. Low solubility with amoxicillin for example can result in a homogenous lump of powder floating unused in the main header tank or leading to blockage of water proportioners (L. Reeve-Lolinson, *The Pig Journal* 1998, 42, 74-86).

Research work has demonstrated that for the administration of benzimidazole compounds via the drinking water a very robust carrier system has to be used. The invention described hereafter demonstrates that a "Solid in Oil in Water" emulsion with specifically selected excipients provides an excellent carrier for the presented problem.

Normally, water insoluble veterinary drugs are administered in dry form through one of the following routes:
 mixed into a dry feed blend, pelletised or not, and subsequently fed to the target animals of interest as a medicated feed
 mixed with a special ingredient composition which may be pelletised or not as a medicated premix. This premix is dosed by the farmer on top of the normal feed supplied to the animals.

These routes for medication are becoming less popular, due to the possibility of contamination of other feed blends with the active compound in the blending and transport equipment at the production facility, usually a feed mill. Another problem related to these routes of medication is the difficulty for the end-user, normally the farmer, to control the dosage of active compound per animal. In case of medicated feeds in mash form or medicated premixes in powder form the farmer can also be exposed to the active compound, which may pose health risks.

In case of liquid dosage of water-insoluble veterinary drugs, only trivial formulations for batch wise liquid dosage are described, with a limited stability. These formulations are not suitable for a reliable and reproducible dosage in a water distribution system. The problem is the impossibility to add these insoluble active compounds directly into the drinking water supply system, without occurrence of precipitation or creaming of the active compound in the storage vessel or in the water pipes during practical time scales of 3 up to 12 hours normally used in drug administration through drinking water systems. Up to the present no convenient solution was available for this route of medication of farm animals for water insoluble veterinary drugs.

DESCRIPTION OF THE INVENTION

The present invention provides a solution to these problems by presenting a new formulation method, which results in a product with such characteristics that it is suitable for administering the water insoluble active compound through the drinking water systems presently used in animal keeping and/or production facilities.

According to the invention a method is described for the preparation of a stable veterinary formulation which is suitable for controlled dosage of a water insoluble veterinary drug or a mixture of water soluble and insoluble veterinary drugs in drinking water distribution systems used in animal husbandry. The method comprises mixing the active compound with a water-immiscible liquid in such a manner that the mixture of active compound and water-immiscible liquid has a density which near to the density of water, and suspending the mixture in an aqueous carrier. The method is further characterised by the features of the appending claims. The invention also provides an emulsion which can be prepared according to this method and which is suitable for administration through the drinking water supply.

Through this new formulation the veterinary drug or a mixture of veterinary drugs, alternatively called "active compound" can be delivered to the target animal
- through a water tank containing the active compound, which is connected to the common or individual water dispensers which supply water to the animals, or
- through a high or low pressure water circuit with individual water nipples.

The active compound can be dosed into the water system of choice by means of mixing and diluting the formulation with water in the central water tank or separate storage tank. Alternatively the formulation is injected continuously into a high or low pressure ring system for water distribution, using a dosage dispenser. The formulation has a considerable storage stability up to two years and shows a surprising good "in use" stability in each type of water distribution system. In case of the water tank dosage system, the formulation with the concentrated active compound can be dosed directly in the tank to obtain the desired concentration level for medication in the water distribution system. In case of an in-line dosage system, a pre-dilution of the original formulation will stay stable in the dispenser unit and also during and after the high shear injection into the water distribution net until the final uptake by the target animal. With this new formulation no fouling and clogging of the distribution system is observed and a very constant level of active compound is measured at the outlet, which is a prerequisite for an adequate uptake by the target animals.

Other advantages of the new formulation technique for liquid dosage suspoemulsion is the simplicity and thus the low costs of preparation, the possibility to combine different active compounds in this formulation and the ease of incorporating other adjuvants (liquid or solid). Also the absence of unwanted solvents used for solubilising water insoluble active compounds like N-methylpyrrolidone [EP 427582, Crook, M. J.] is advantageous. All the ingredients needed for preparation of the suspoemulsion, comply with the recommendations described in the note for guidance: *Development of Pharmaceutics for Veterinary Medicinal Products in Europe* [Directive 81/852/EEC].

The suspoemulsion formulations according to the present invention can be obtained as follows: The active water insoluble compound (or the mixture of active compounds) of interest is normally available in the form of a powder with a small particle size distribution, preferably in the range between 0 and 100 μm and more preferably with a particle size ranging about 1 μm to about 30 μm, especially from 4 to 20 μm, as can be determined by the usual techniques like for example static light scattering measurements. An example of active compounds of interest are the anthelmintics, more specifically the benzimidazole derivatives, which normally show a very limited solubility in water. Their levels of administration through a water distribution system, normally range between 0.01 and 1 wt. % of active compound, which can be obtained by dilution from a concentrated suspoemulsion through the different water distribution systems described before.

In a preferred embodiment of the invention, the active compound can be suspended at a level ranging between 1 and 90 wt. % active compound, more preferably between 10 and 30 wt. %, into a suitable water immiscible liquid. The water immiscible liquid selected, normally shows a good affinity with the solid particles of the active compound, facilitating a good wettability of the solid particles. In the event of limited wettability of the active compound powder, wetting agents like for example lignosulphonates and non-ionic ethoxylates can be used. Normally these compounds are not necessary with the preferred method of formulation.

Depending on the density of the active compound, the water immiscible liquid, preferably, has a density, which compensates for the density of the active compound. This leads to a combined specific density of the solid-immiscible liquid aggregate which is, more or less, equal to the density of water (regarded to be 1000 kg/m$^3$). This will slow down the creaming or precipitation of the active compound during storage and usage. In case the active compound has a mean density higher than 1000 kg/m$^3$, a water immiscible liquid with a density lower than 1000 kg/m$^3$ is preferably used. In case of an anthelmintic like Flubendazole® with a density of 1420 kg/m$^3$, an oil can be selected like sunflower oil with a density of approximately 920 kg/m$^3$. In case of an active compound with a density below 1000 kg/m$^3$, an immiscible liquid with a density higher than 1000 kg/m$^3$ may be selected, like for example sucrose acetate isobutyrate, silicon oil or brominated vegetable oils. The preferred volume of water immiscible liquid needed for obtaining an overall density of 1000 kg/m$^3$ can be calculated by formula 1:

$$V_{wil} = (1000/\rho_{ac} - 1) * M_{ac}/(\rho_{wil} - 1000) \quad (1)$$

$V_{wil}$=Volume of water immiscible liquid (m$^3$) needed.
$M_{ac}$=Mass active compound (kg).
$\rho_{ac}$=Density of active compound (kg/m$^3$).
$\rho_{wil}$=Density of water immiscible liquid (kg/m$^3$).

The ratio between water immiscible liquid and active compound obtained with formula 1, describing the density compensation principle, is not imperative for the choice of the actual levels used in the formula. They also depend on the practical demands stated for the commercial formulation of choice. For example, legislative, pharmaceutical or other demands and the presence of a mixture of water insoluble, active compounds could prevent the use of the density compensation principle described before. The water immiscible liquid phase could even have the same low or high density, relative to the water phase, as one or more of the selected active compounds. In this case the resulting suspoemulsion can be protected against physical destabilisation processes by using proper emulsifier and/or thickener ingredients as described later. In general a deviation from unit density from −15% to +20%, in particular of +5% can be accommodated, if necessary with the use of suitable emulsifiers and/or thickeners etc.

Also for the storage stability at low temperatures around 0-10° C. special precautions have to be taken, when selecting the water immiscible liquid phase, in order to prevent possible crystallisation effects of this liquid. Crystallisation would lead to a destabilisation of the suspoemulsion system. For vegetable oils, this implies that an oil containing higher levels of triglycerides with a lower chain length should be selected. For the suspoemulsion prepared, even freeze-thaw stability was observed for one freeze thaw cycle.

In order to obtain a suitable suspension of the active compound into the water immiscible liquid, several mixers can be used, for example pumps in parallel with a tank, colloid mills, high pressure homogenisers and other industrially relevant configurations.

To obtain the final formulation, in which the particles are coated with a suitable amount of the water immiscible liquid, the freshly prepared suspension is emulsified into a water phase, using a mixing device, which supplies enough energy to get the proper wetting of solid, yielding a mean specific density of the water immiscible liquid-active compound aggregate around 1000 kg/m$^3$. For this purpose, again the same instrumental configurations as used for the preparation of the suspension can be used. In fact, the solid phase-water immiscible liquid phase is emulsified into the water phase, yielding a so called suspoemulsion [Knowles, D. A., *Chemistry and Technology of Agrochemical Formulations*, Dordrecht, Kluwer Academic Publishers, 1998, 440p. ISBN 0-7514-0443-8]. Normally elevated energy densities are used, preferably ranging between 10-50 MJ/m$^3$, using one or multiple stage mixing treatments. The homogenisation treatment does not cause a change in particle size distribution of the water-insoluble active compound. The ratio of solids, water-immiscible liquid and water can be chosen based on the rheological demands posed by the dosage and drinking water systems and the density compensation principle described before. Normally the formulation is optimised to the highest level of the active compound practically possible.

To stabilise the freshly prepared suspoemulsion against heteroflocculation and coalescence, optionally an emulsifying agent can be added, depending on the intrinsic stability of the system and the storage and "in use" stability required. For the emulsifier, a wide range of suitable ingredients and commercial mixtures of ingredients can be selected, ranging from protein products like casein or whey protein isolate and their hydrolysates, carbohydrate based emulsifiers like gum arabic or small molecules like citric acid esterified mono-or diglycerides of fatty acids. The selection of the right emulsifier depends on the exact nature of the water immiscible liquid of interest and the droplet size needed around the solid phase. Normally, the emulsifier is solubilised in the water phase or the water insoluble liquid phase before processing at the dosage levels recommended by its supplier.

The obtained suspoemulsion can be stabilised even better against destabilisation due to physical processes like coalescence, heteroflocculation, creaming or precipitation, by adding suitable thickeners like cross-linked polyacrylic acids, chemically modified starches or hydro-colloids like xanthan, carrageenan or other gums, propylene glycol alginate, methyl cellulose and many other commercially available thickeners. Depending on the textural needs and wants and the stability performance required for the veterinary drug formulation, the thickener or a mixture of thickeners can be selected by a skilled person. The preferred thickener in case of active compounds like anthelmintics is xanthan, giving the product a high yield stress at dosage levels preferably ranging between 0.2 and 0.4 wt % on total product, thus preventing the solid particles to flocculate, cream or precipitate under practical storage conditions.

Long term stability against chemical degradation can be improved if needed, by selecting a stable water immiscible liquid. In case of a vegetable oil, this implies an oil with a low content of unsaturated bonds in the fatty acid chains and high levels of anti-oxidative compounds, like tocopherols. Also anti-oxidative additives can be added to the water and/or water immiscible liquid phase in order to improve the stability of different constituents. Non-limiting examples for oxidation-limiting additives are salts of ethylenediamine-tetraacetate (EDTA), typically at a level of 40-200 ppm, e.g. 100 ppm, and citric acid (0.1-0.5% range) which can be added to the water phase. Monoglyceride citrate (20-100 ppm range) or tocopherols, butylated hydroxytoluene and butylated hydroxyanisole (100-200 ppm range) can also be added to the water-immiscible phase prior to the processing.

Finally the stability of the veterinary drug formulation against microbial spoilage can be improved by adding antimicrobial additives to the water and/or the water immiscible phase and/or by changing the pH to the best growth-inhibiting level. Some examples of anti-microbial active compounds are parabenes, sodium benzoate and potassium sorbate, which can be dissolved in the water phase before processing at their active levels.

EXAMPLE 1

Preparation of Aflubendazole Suspoemulsion

For the preparation of a veterinary drug formulation the anthelmintic flubendazole was selected as the water insoluble active compound. For the water immiscible liquid a high oleic sunflower oil (HOZOL) was selected with a melting point of 0° C. 100 grams of flubendazole were dispersed in 384 ml HOZOL oil by adding the flubendazole to the oil under stirring with an ultraturrax mixer. The water phase was prepared by making an 1 liter aqueous buffer having the following composition (dosage in wt %): Citric acid (1 wt. %), potassium sorbate (0.1 wt. %), sodium benzoate (0.1 wt. %), disodium ethylenediamine-tetra-acetate (0.01 wt. %), and 2M Sodium hydroxide solution; the pH was adjusted to 5.

365 ml of the aqueous buffer was mixed with 150 grams of gum arabic and 2.5 grams of xanthan under stirring and this mixture was added to the oil phase containing the flubendazole, while it was stirred with an ultraturrax. The aqueous buffer was added to obtain a total volume of 1 liter of suspoemulsion with a total flubendazole content of 10% (w/v). Finally, the crude suspoemulsion was homogenised at 500 bars by passing the preparation in three subsequent cycles through a high pressure homogeniser.

This preparation was studied for its stability under storage conditions and for "in use" situations as described in example 2.

EXAMPLE 2

Stability Evaluation of the Separate Suspoemulsions Under Storage Conditions and "In Use" Situations In order to evaluate the stability of the suspoemulsion made as described under example 1, the storage stability and the "in use" stability was determined for the suspoemulsion as such and for a 0.01 wt % dilution in tap-water, based on the flubendazole content, respectively. The 0.01 wt % dilution is relevant for the diluted situation of the suspoemulsion in the water distribution system, where it normally has an estimated residence time of maximally 3 hours.

The stability of both preparations was monitored in time by measuring destabilisation phenomena like creaming or precipitation with the help of a macroscopic optical scanning device called "Turbiscan" supplied by Formulaction, France. The 0.01 wt % flubendazole diluted suspoemulsion was measured at 0, 3 and 17 hours.

Additionally, the particle size distribution of the original suspoemulsion was determined by static light scattering measurements using a 45 mm lens and tap-water. The stability of the undiluted suspoemulsion as measured by static light scattering measurements was followed over a period of 8 months. The results from the Turbiscan scan measurements were evaluated graphically. These results show that a 10 wt. % flubendazole suspension as described above exhibits no detectable destabilisation effect in comparison with a non-stabilised 10 wt. % flubendazole suspension. A 0.01 wt. % diluted suspoemulsion does not show an important creaming or precipitation effect within 17 hours, compared with a free 0.01 wt. % suspension of flubendazole respectively. This implies that the diluted product stays stable under static conditions, like for example in the dosage tank of an automatic injection system.

The results from the particle size measurements are collected in table I. Table I also supports the finding that the non-diluted suspoemulsion is a very stable formulation, showing no coalescence or heteroflocculation processes over a period of 8 months.

TABLE I

Particle size distribution of a suspoemulsion, containing flubendazole (Fb), as a function of time.

| Preparation | particle size distribution at t = 0, (D[3, 2] in μm). | Particle size distribution at t = 8 months, (D[3, 2] in μm). |
|---|---|---|
| 10 wt % Fb suspoemulsion | 0.99 | 1.00 |
| Fb powder | 1.53 | — |

The invention claimed is:

1. A method of preparing a suspoemulsion suitable, optionally after dilution, for administering flubendazole through a water distribution system, comprising mixing flubendazole with a water-immiscible liquid in such a manner that the mixture of active compound and water-immiscible liquid has a density between 0.85 and 1.2, and suspending said mixture in an aqueous carrier.

2. A method according to claim 1, in which the flubendazole and the water-immiscible liquid are used in a weight ratio between 10:90 and 75:25.

3. A method according to any one of claim 1 or 2, in which the water-immiscible liquid has a lower density than water.

4. A method according to any one of claim 1, 2 or 3, in which said mixture or the suspension thereof in the aqueous carrier comprises one or more stabilising agents belonging to the group of emulsifiers, surfactants, thickeners, anti-oxidants and anti-microbials.

5. A method according to any one of claim 1, 2, 3 or 4, in which said water-immiscible liquid is a vegetable oil.

6. A method according to any one of claim 1, 2, 3, 4 or 5 in which the average particle size of the flubendazole is between 1 and 30 μm.

7. A suspoemulsion suitable, optionally after dilution, for administering flubendazole through a water distribution system, comprising a homogeneous suspension in water of a mixture of the flubendazole and a water-immiscible liquid, said mixture having a density between 0.85 and 1.2.

8. A suspoemulsion according to claim 7, comprising one or more of the following features:

a) the flubendazole and the water-immiscible liquid are used in a weight ratio between 10:90 and 75:25;

c) the water-immiscible liquid is a vegetable oil;

d) the suspoemulsion comprises one or more stabilising agents selected from emulsifiers, surfactants, thickeners, anti-oxidants and anti-microbials;

e) the weight ratio between said mixture of flubendazole, a water-immiscible liquid and said water is between 80:20 and 10:90;

f) the density of the mixture of flubendazole and water-immiscible liquid is between 0.95 and 1.05.

* * * * *

UNITED STATES PATENT AND TRADEMARK OFFICE
CERTIFICATE OF CORRECTION

PATENT NO.        : 9,040,571 B2                                              Page 1 of 1
APPLICATION NO.   : 12/259844
DATED             : May 26, 2015
INVENTOR(S)       : Ekhart et al.

It is certified that error appears in the above-identified patent and that said Letters Patent is hereby corrected as shown below:

In the List of References Cited:
Title page, column 2, line 6, delete "Parazitologiiya" and insert --Parazitologiya--.

In the Claims, Claim 8:
Column 8, line 35 (approximately), delete "c)" and insert --b)--.
Column 8, line 36 (approximately), delete "d)" and insert --c)--.
Column 8, line 39 (approximately), delete "e)" and insert --d)--.
Column 8, line 42 (approximately), delete "f)" and insert --e)--.

Signed and Sealed this
Thirteenth Day of October, 2015

Michelle K. Lee
*Director of the United States Patent and Trademark Office*